United States Patent [19]
Hugentobler

[11] Patent Number: 5,808,201
[45] Date of Patent: *Sep. 15, 1998

[54] ACOUSTIC STRAIN GAUGE

[75] Inventor: Monte K. Hugentobler, Novato, Calif.

[73] Assignee: SonicForce, L.L.C., Burlingame, Calif.

[*] Notice: The term of this patent shall not extend beyond the expiration date of Pat. No. 5,750,900.

[21] Appl. No.: 707,922

[22] Filed: Sep. 9, 1996

[51] Int. Cl.⁶ .................................................. G01N 29/24
[52] U.S. Cl. .................................. 73/643; 73/597; 73/779
[58] Field of Search ............................. 73/643, 597, 598, 73/779, 599, 600; 324/209

[56] References Cited

U.S. PATENT DOCUMENTS

| | | |
|---|---|---|
| 3,850,028 | 11/1974 | Thompson et al. . |
| 3,877,294 | 4/1975 | Shaw . |
| 4,013,905 | 3/1977 | Breneman et al. . |
| 4,048,847 | 9/1977 | Alers et al. . |
| 4,080,836 | 3/1978 | Thompson et al. . |
| 4,092,868 | 6/1978 | Thompson et al. . |
| 4,104,922 | 8/1978 | Alers et al. . |
| 4,127,035 | 11/1978 | Vasile . |
| 4,184,374 | 1/1980 | Thompson et al. . |
| 4,218,924 | 8/1980 | Fortunko et al. . |
| 4,232,557 | 11/1980 | Vasile . |
| 4,246,793 | 1/1981 | Fairand et al. ............................. 73/628 |
| 4,248,092 | 2/1981 | Vasile et al. . |
| 4,344,663 | 8/1982 | Ognier et al. . |
| 4,593,567 | 6/1986 | Isselstein et al. . |
| 5,085,082 | 2/1992 | Cantor et al. ............................. 73/622 |
| 5,170,366 | 12/1992 | Passarelli ................................. 73/597 |

FOREIGN PATENT DOCUMENTS

0031639   3/1981   Japan ...................................... 73/643

Primary Examiner—Hezron E. Williams
Assistant Examiner—Rose M. Miller
Attorney, Agent, or Firm—Coudert Brothers

[57] ABSTRACT

Applicant's invention defines an improved electromagnetic acoustic transducer (EMAT) for monitoring stress in an underlying workpiece. The EMATs are provided with positioning pins for fixing the registration of the EMAT relative to the workpiece. The bottom contact surface of the EMAT may be altered geometrically or provided with a friction reducing means, such as a wheel assembly, to minimize contact surface area and thus unwanted frictional influences caused by deformation of the workpiece under the EMAT. An apparatus for reliably positioning the EMATs above a workpiece is also disclosed, said apparatus comprising an actuating means which by a linkage mechanism lowers or raises at least one EMAT into position, further allowing access to the positioning pins for applying the necessary force to anchor the EMATs to the workpiece.

12 Claims, 9 Drawing Sheets

ACOUSTIC STRAIN GAUGE

FIELD OF THE INVENTION

The present invention relates to the field of devices for measuring stress. More particularly, the invention relates to the measurement of stress by determination of the speed of acoustic waves in a material. Assignee is also the assignee of an improved electromagnetic acoustic transducer which is disclosed in U.S. Pat. No. 5,503,020 issued Apr. 2, 1996.

BACKGROUND OF THE INVENTION

Conventional resistance strain gauges measure the microstrain directly under the footprint of a small resistance gage bonded to a prepared surface of a material of interest. As the material deforms, the resistance of the strain gauge changes, and a calculation of applied strain may be made of the measured material based on known characteristics. Because such measurements are confined to the immediate surface to which the strain gauge is bonded, the measurement is very discreet and does not necessarily represent the condition of the examined specimen in other areas of close proximity. The test technician in such a case, must choose the location of the strain gauge carefully, in reliance on the assumption that neighboring conditions are the same as those found in the detection area. What is needed is a measurement device which can be moved easily to measure greater areas of a material than those measured by conventional resistance strain gauges.

To prepare a structure for placement of a resistance-based strain gauge, the surface of the structure is usually prepared by removing paint and rust (sometimes by sandblasting), and by grinding and polishing the surface. The preparation for attaching such a gauge necessarily requires significant labor. In cases where the structure to be examined is a structural beam of, for example an older bridge, there is a likelihood that lead paint will have to be removed, an environmentally sensitive task. After laboriously preparing the surface of the structure to be analyzed, some kind of bonding medium is applied to the detection surface to affix or locate the resistance strain gauge to obtain good data. Dramatic reductions in test costs could be realized if data representing stress and strain could be obtained with limited surface preparation of the material to be analyzed.

A further limitation associated with utilizing conventional resistance strain gauges for measuring stress in bridges or other structures is that only measurements of surface stress or strain are detectable. Consequently, stresses or flaws underneath the immediate surface go unmeasured, and the technician evaluating the data must make critical assumptions about the overall integrity of the structure being examined based solely on the condition of its surface. What is needed then is a stable stress detection method which provides data at a greater depth than that produced by conventional resistance strain gauges.

To assist in solving these problems, acoustic instruments have been employed to measure stress and strain by measuring the time of flight of an acoustic wave through the material. Factors which can affect the measurement of a wave's time of flight ("TOPF") include, but are not limited to: material properties such as texture, i.e., grain size and orientation; geometry of the specimen; and temperature.

One method of measuring stress or strain with acoustic instruments employs two or more orthogonal acoustic wave modes and/or measurement directions to cancel the aforementioned predominant unwanted effects. To date, either piezo-electric transducers or electromagnetic acoustic transducers ("EMATs"), have been employed in measuring TOF.

As set forth in Assignee's aforementioned U.S. patent, an EMAT generally comprises a conductor which is positioned within a static "biasing" magnetic field (B) near the surface of a conducting material. When an alternating current ($I_\omega$) is applied to the conductor, eddy currents ($J_\omega$) are induced within the surface layer of the conducting material. These induced eddy currents, in the presence of a biasing magnetic field, result in a Lorentz force which deflects the moving electrons in a direction defined by the vector product of $J_\omega \times B$. The electrons then collide with the ions in the lattice structure of the conducting material, ultimately generating acoustic energy in the form of an ultrasonic wave that propagates through the metal structure. The velocity (v) of the ultrasonic wave is determined by the scalar product of its wavelength ($\lambda$) and its frequency (f), i.e., $v = \lambda \cdot f$. The frequency of the ultrasonic wave is determined by that of the applied alternating current induced into the coil of the receiving EMAT. Additionally, the orientation of both the biasing magnetic filed and the induced eddy current determine the direction and mode characteristics of the propagating energy, and may be varied depending on how a technician wishes to examine a material, as well as the properties and configuration of the material itself.

EMATs have been fabricated with a variety of coil and magnet configurations to suit the requirements of particular applications. The teachings of U.S. Pat. Nos. 3,850,028, 4,048,847, 4,080,836, 4,092,868, 4,104,922, 4,127,035, 4,184,374, 4,218,924, 4,232,557, 4,248,092, 4,344,663 and 4,593,567, which are incorporated herein by reference, illustrate some of the configurations of electromagnetic acoustic transducers, their application and their limitations.

In the case of continuous monitoring of stress using EMATs, care must be taken to compensate for any change in length under the EMATs and along the wave path due to deformation of the test piece. As the metal under the EMAT is subjected to loading and unloading, it either elongates or compresses. As the metal to be tested expands or contracts, it moves under the EMAT. This motion causes the EMAT to shift its position on the metal. Exactly where the EMAT will be positioned on the metal as it moves and after it moves is unpredictable; however, it is likely that the EMAT will shift position due to such moves. Under typical conditions, an EMAT can shift along the wave path, typically the longitudinal axis of the test material, or if the contact with the metal is asymmetric, the EMAT may also rotate. Changes in position of the EMAT as small as one millionth of an inch will cause errors in acquired data.

It is an object of the present invention to measure the applied stresses in a structure by measuring the relative times of flight of single acoustic wave forms with electromagnetic acoustic transducers having a fixed footprint, i.e., each EMAT remains precisely positioned above the test surface regardless of any change in length in said test piece along the test wave path.

Today, many EMAT's are constructed with a flat bottom which rests on the workpiece to be analyzed. During the aforementioned stress and strain which occurs in the workpiece, the amount of contact surface area comprising the bottom of a flat EMAT affects the movement of the EMAT on the workpiece. To date, no prior art teaches a method or EMAT configuration for minimizing the contact area of an EMAT bottom, nor is any other method of minimizing friction between the EMAT contact area and the workpiece known. Also, no prior art teaches a technique to anchor or fix EMATs to the surface of the workpiece.

It is an object of the present invention to minimize unwanted frictional forces between the EMAT bottom or contact surface and the workpiece to minimize movement of the EMAT relative to the workpiece.

It is yet another object of the present invention to provide a way to establish the EMAT in fixed registry with the workpiece to be analyzed.

SUMMARY OF THE INVENTION

Broadly stated, the present invention encompasses a method of fixing one or more EMAT transducers (typically one to transmit and one to receive) to a specimen or workpiece to be tested. The transmitting EMAT introduces energy into the specimen at the instant a high speed counter, indexed to the zero crossing of the measured wave signal, begins operation. The acoustic energy traverses the distance to the receiving EMAT, where it is detected and converted into an electrical signal. The termination of the measurement event is indexed to an area of the detected wave such as its zero crossing, or other readily recognizable portion of the electrical signal of the detected wave. The time differential represents the TOF of the acoustic tone burst.

To measure applied stresses, the specimen is measured in an unstressed condition and then in a stressed condition. The change in TOF is calculated and stored. Typically, the change in TOF of a specimen under stress versus its unstressed condition is a function of: 1) the direction of the principal stresses relative to the measurement direction used; 2) specimen elongation, or strain; 3) velocity changes due to acoustoelasticity; and 4) temperature. However, as long as the combination of these effects is predictable and subject to limitations based on the structural material in question and its geometry, the TOF comparison can be relied on as a reliable source of information for measuring actual applied stresses.

In particular, the improved EMAT of the invention comprises an EMAT body having affixed to it a pin in general alignment with the EMAT's longitudinal axis. The pin extends a predetermined distance beyond the EMAT body's bottom plane. The pin has an upper end for striking and a pointed end, which is in contact with the workpiece directly thereunder. The EMAT body also has affixed to it a friction reducing means for engaging the workpiece and for supporting the EMAT thereon. When the pin is struck, the pin indents the workpiece locating the bottom plane of the EMAT is substantially coplanar registry therewith. The friction reducing means prevents surface deformations occurring in the workpiece from affecting the registry of the EMAT on the workpiece.

In another embodiment of the present invention, an EMAT configuration employing rails on the bottom contact surface, extending in the direction of the anticipated workpiece strain are provided to minimize unwanted frictional forces.

In yet another embodiment of the present invention, roller bearings provide the contact surface on the underside of the EMAT to facilitate movement, while the pins affixed to the EMAT maintain the registry between the transducer and the workpiece.

It is anticipated that the pins or pointed positioners may be affixed to the EMAT by several means, for example: welding to the EMAT body or frame; being attached in a bushing which is sized to retain said positioner in position against the EMAT body or frame; retained in a housing with a latching means such that the pin is locked into position against the EMAT after having traveled a predetermined distance toward and into said workpiece. Suffice it to say a variety of methods may be employed to affix the pins or positioners to the EMAT to accomplish the purpose of indenting the workpiece and anchoring the EMAT.

The present invention utilizes a simple extension of the EMAT body to house two wheel assemblies comprising a shoulder screw passing through a wheel bearing. The steel cover atop the EMAT body, which also completes the magnetic circuit of the EMAT extends beyond the body, and has a conventional threaded center punch as a positioning pin engaged therein which extends past the bottom plane of the EMAT body. When the pin is struck, its hardened lower point engages the beam or workpiece underneath, and establishes the bottom plane of the EMAT in coplanar registry therewith.

In an embodiment of the present invention, two EMATs may be positioned on a workpiece to continually monitor applied stress by utilizing a mechanism operably connected to the EMATs and housed in a chassis. An actuating means raises or lowers the mechanism, locating the EMATs on the workpiece where they can be anchored by their pins. Such an actuating mechanism can by mechanical or electronic, simply serving to work the mechanism to raise or lower the EMATs onto the workpiece. The chassis also provides a structure for mounting a temperature sensor for correction data used in analyzing and processing the data generated by the EMATs. The chassis also provides support for pc boards and a computer interface connection for transmitting data to a computer. If desired, the chassis may be fitted with one or more magnets to help located the chassis on a workpiece prior to lowering the EMATs into position. In such a configuration, a second set of positioning pins may be provided to affix the chassis to the workpiece as well as the EMATs.

In a preferred embodiment, a chassis is also provided with an actuating handle and a mechanism (currently a plurality of links) which allows one or more EMAT to be lowered by a lifting post and lifting lug into position directly above a workpiece. Where two EMAT assemblies are used, they are positioned a distance apart, and that distance is set by striking the positioning pins of each EMAT assembly. Currently, the chassis is approximately 12" long and 4.5" wide, constructed of aluminum. The linkages are also aluminum to minimize weight. An actuating handle operates the positioning mechanism, and the positioning pins for the EMAT assemblies as well as the chassis itself are available through the top of the chassis. Pc boards are enclosed in the chassis to process information from the EMATs and a temperature sensor for compensating calculations are in communication with the pc boards. A computer interface connection is provided in one end of the chassis for transmitting data to a computer for further analysis.

The bottom contact surface of the EMAT may be altered geometrically to minimize the contact surface area and thus unwanted frictional influences, or may be fabricated with a friction reducing means such as a wheel assembly or roller bearings, to allow deformation of the workpiece under the EMAT without compromising the registry between the two.

DETAILED DESCRIPTION OF THE INVENTION

Figure 1:
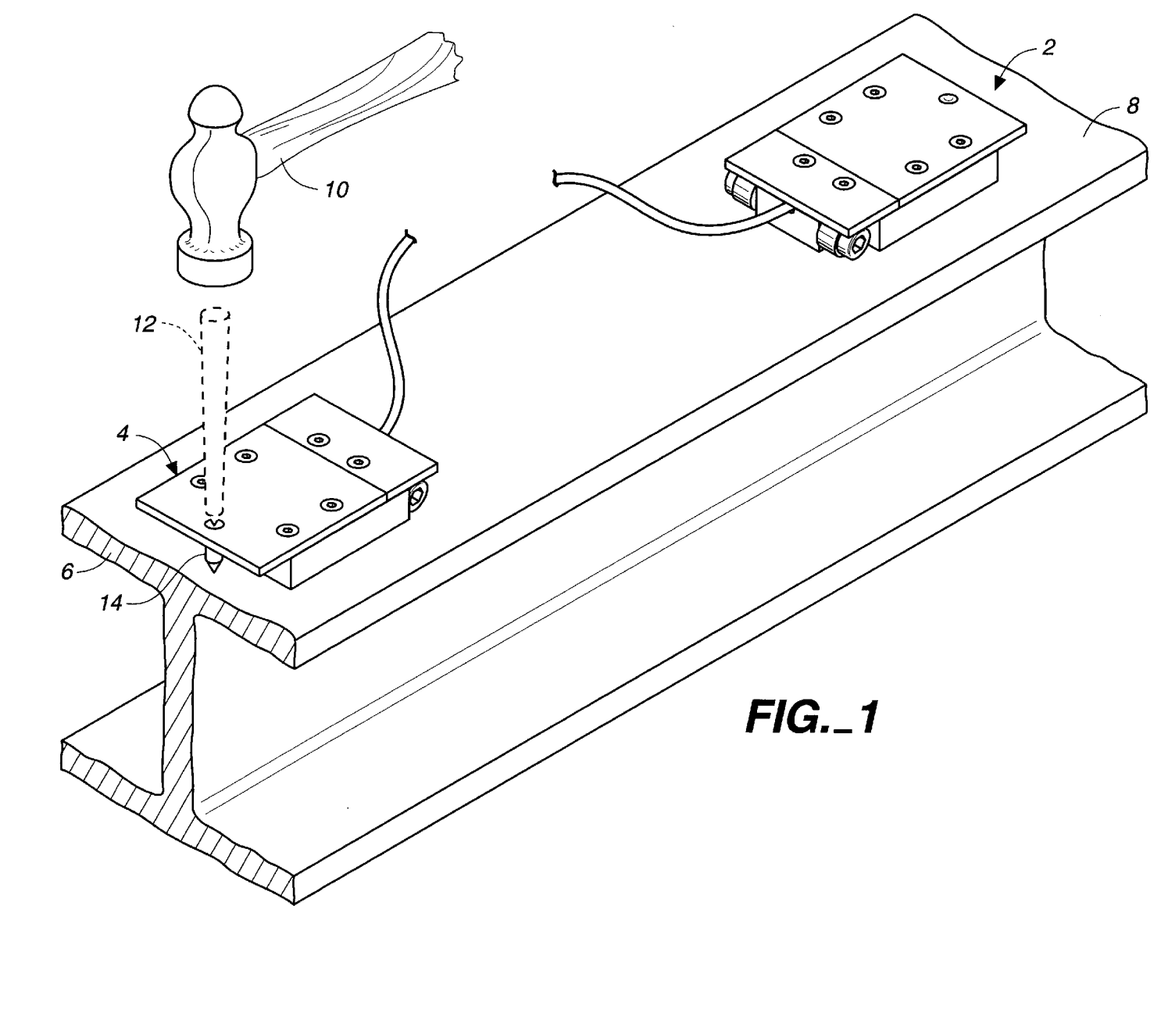
FIG. 1 is a perspective of the basic invention of two separate electromagnetic transducers being located by striking a punch integral to each device with a hammer.

FIG. 1 shows the positioning of two EMAT assemblies, 2 and 4 on a metal beam 6. Typical of most structural beams used in structural applications outdoors, a coating of paint 8 has been applied to beam 6 to prevent corrosion. A hammer 10 is shown in position to strike punch 12, thereby driving positioning pin 14 through paint coating 8 and into beam 6 as further illustrated in FIG. 3B.

Figure 2A:
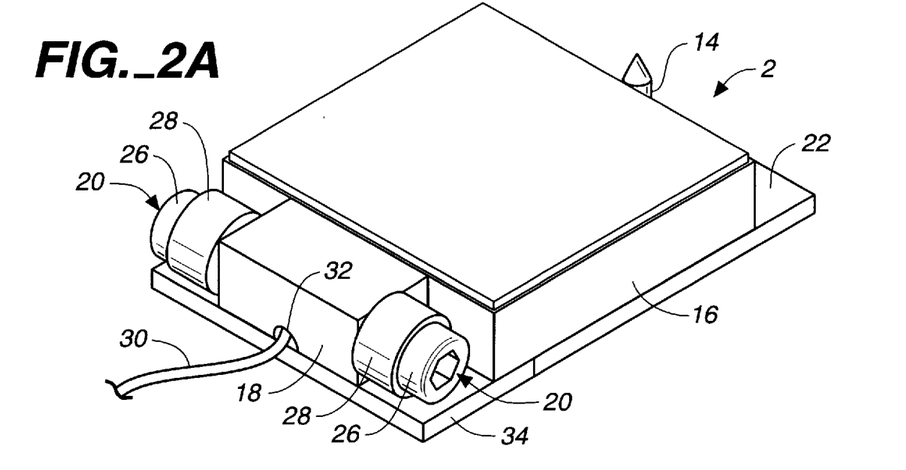
FIG. 2A is a perspective of the bottom of one of the electromagnetic acoustic transducers according to the present invention.

In FIG. 2A, the arrangement of either EMAT assembly 2 or 4 is shown in further detail. EMAT assemblies 2 and 4 are comprised of an EMAT body 16 which has an extended portion 18 to provide structure for a pair of wheel assemblies 20. Plate 22 which provides support for positioning pin 14, is constructed of steel and serves to complete the magnetic circuit of the EMAT body 16, as further described in U.S. Pat. No. 5,503,020. Wheel assemblies 20 each comprise a shoulder screw 26 engaged in extended portion 18, securing wheel bearing 28 thereto. A data transmission cable 30 passes through groove 32 of extended portion 18. A cover 34, typically of aluminum, is affixed to extended portion 18 protecting and securing data transmission cable 30.

Figure 2B:
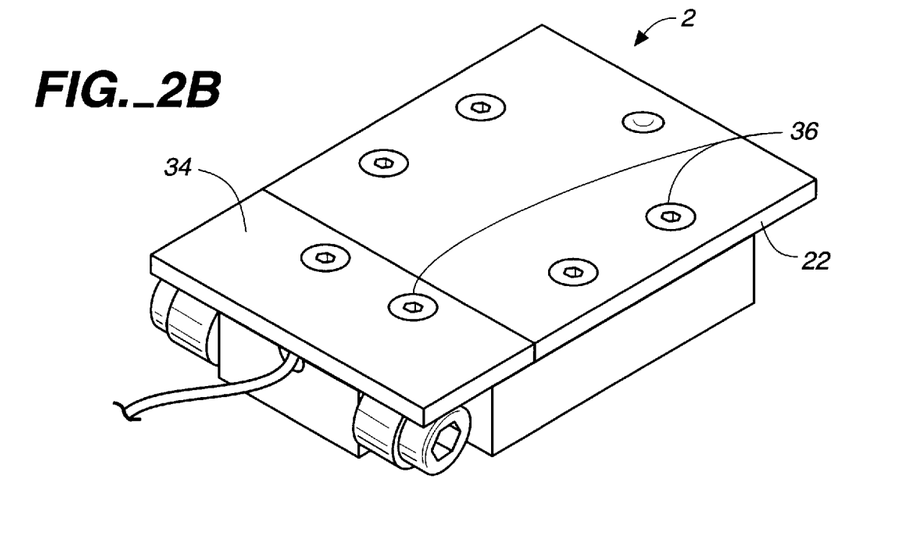
FIG. 2B is a perspective of the top of one of the electromagnetic acoustic transducers according to the present invention.

As shown in FIG. 2B, cover 34 may be affixed to extended portion 18 by a plurality of screws 36, as plate 22 may also be affixed to EMAT body 16. Cover 34 may be affixed to extended portion 18 in any other suitable way to accomplish the purpose of securing and protecting cable 30.

Figure 2C:
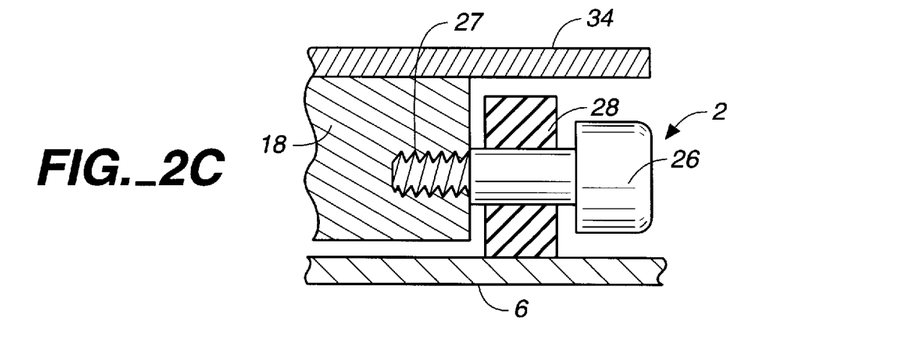
FIG. 2C is a cross-sectional view taken at 2C—2C as shown in FIG. 3A.

FIG. 2C shows a cross-section of extended portion 18. In this figure, tapped hole 27 is shown, with shoulder screw 26 engaged therein, securing wheel bearing 28.

Figure 3A:
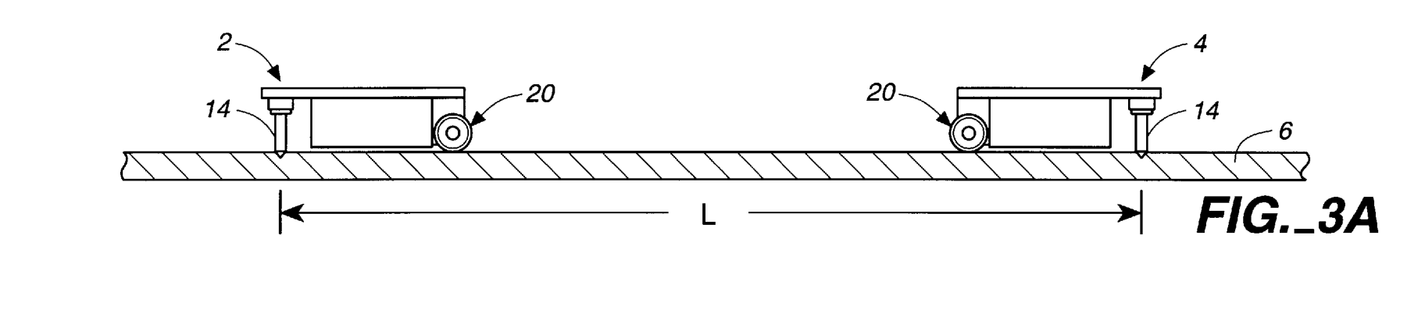
FIG. 3A is a schematic side elevational view of FIG. 2 illustrating a fixed distance between the electromagnetic acoustic transducers according to the present invention.

FIG. 3A represents the positioning of EMAT assemblies 2 and 4 at a specific distance L from each other. As will be further described in FIG. 3B, positioning pins 14 locate EMAT assemblies 2 and 4 in registry with beam 6, said wheel assemblies 20 providing a friction reducing means for allowing the surface of beam 6 to deform in compression or elongation, without changing the registry of either of said EMAT assemblies 2 or 4.

Figure 3B:
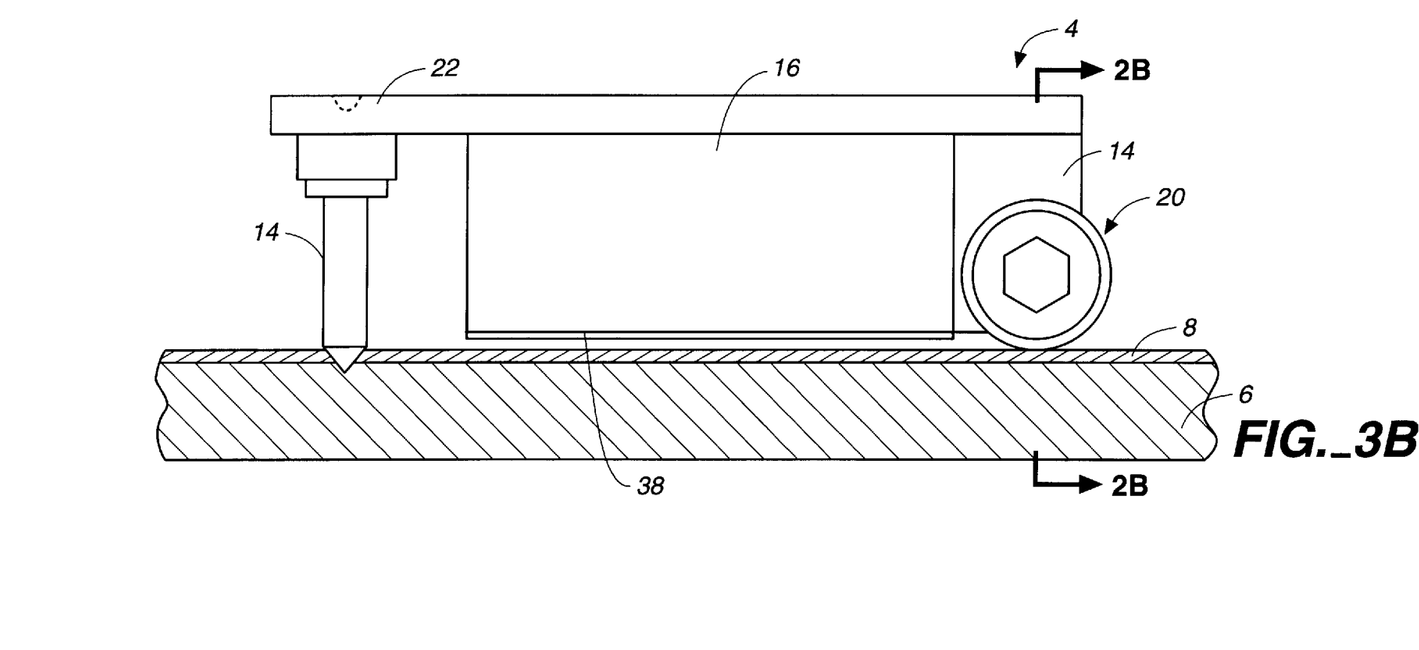
FIG. 3B is an enlarged schematic side elevational view of one of the devices as it would appear on a surface coated with paint.

FIG. 3B illustrates the position of EMAT 2 above a workpiece 10 after positioning pin 14 has been struck, penetrating paint layer 8 on beam 6. Wheel assembly 20 in extended portion 18, in combination with positioning pin 14, establishes bottom plane 38 of EMAT assembly 4 in a substantially coplanar relationship with beam 6. In the embodiment shown in FIG. 3B, positioning pin 14 comprises a threaded commercial punch sized to extend the proper length from plate 22.

Figure 4:
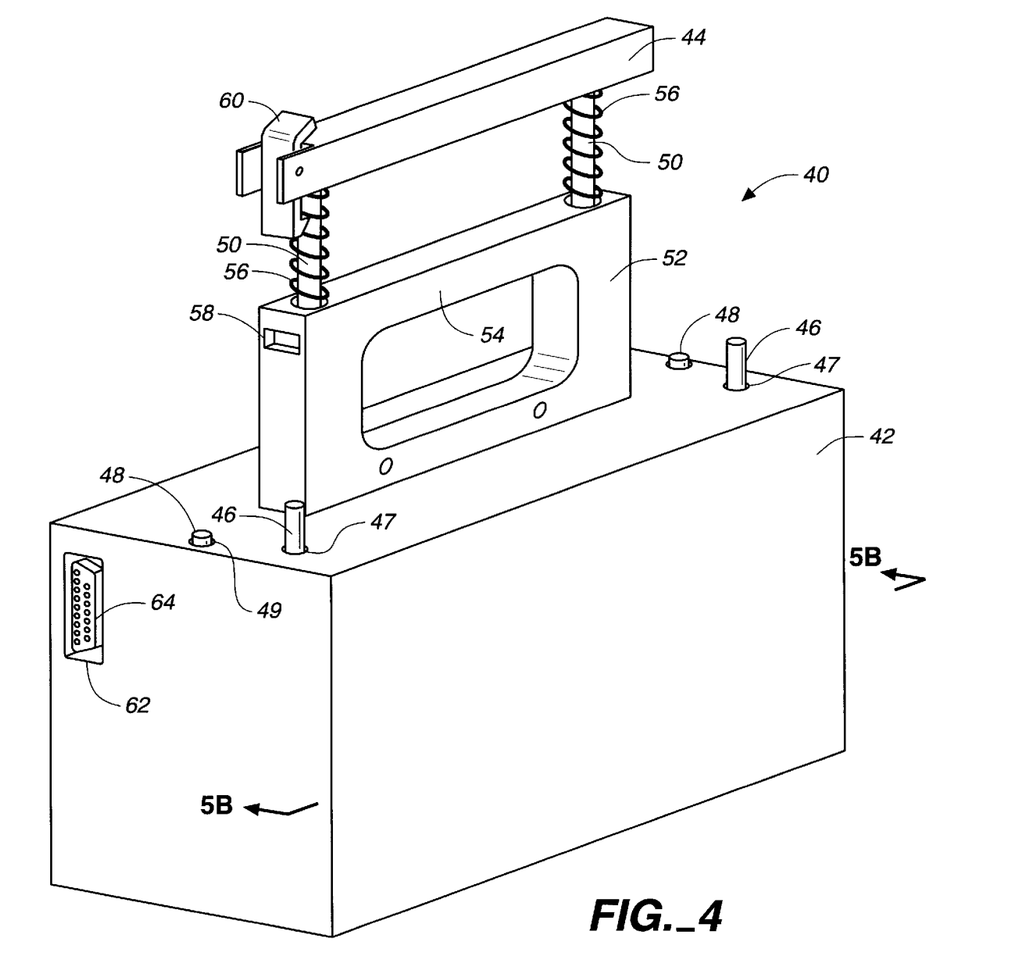
FIG. 4 is a perspective of a unitary housing for the arrangement shown in FIG. 1 with a computer plug port.

FIG. 4 shows an instrument assembly 40, comprising a chassis 42, operated by a handle 44 which is used to reliably position a pair of EMATs above a work piece. FIG. 4 shows the top striking end of two retractable punch extensions 46 and two chassis positioning pins 48, which are utilized to anchor both chassis 42 and the EMATs it houses to an underlying workpiece. Punch extensions 46 extend through a pair of holes 47 in the top wall of chassis 42, and chassis positioning pins 48 extend through a pair of holes 49 provided in the top wall of chassis 42. Handle 44 has two posts 50 extending downward therefrom. Posts 50 extend through a slide 52, which forms a grip 54. A pair of springs 56 bias handle 44 from slide 52. Slide 52 has a notch 58, which is engageable with latch 60 pivotally affixed to handle 44 to retain slide 52 proximate to handle 44. A slot 62 is provided in one end wall of chassis 42 for locating a computer interface connection 64, for transmitting data received by said internal EMAT assemblies. The action of slide 52 up and down posts 50 operates a linkage mechanism to position at least one EMAT assembly above a workpiece, as will now be described in detail.

Figure 5A:
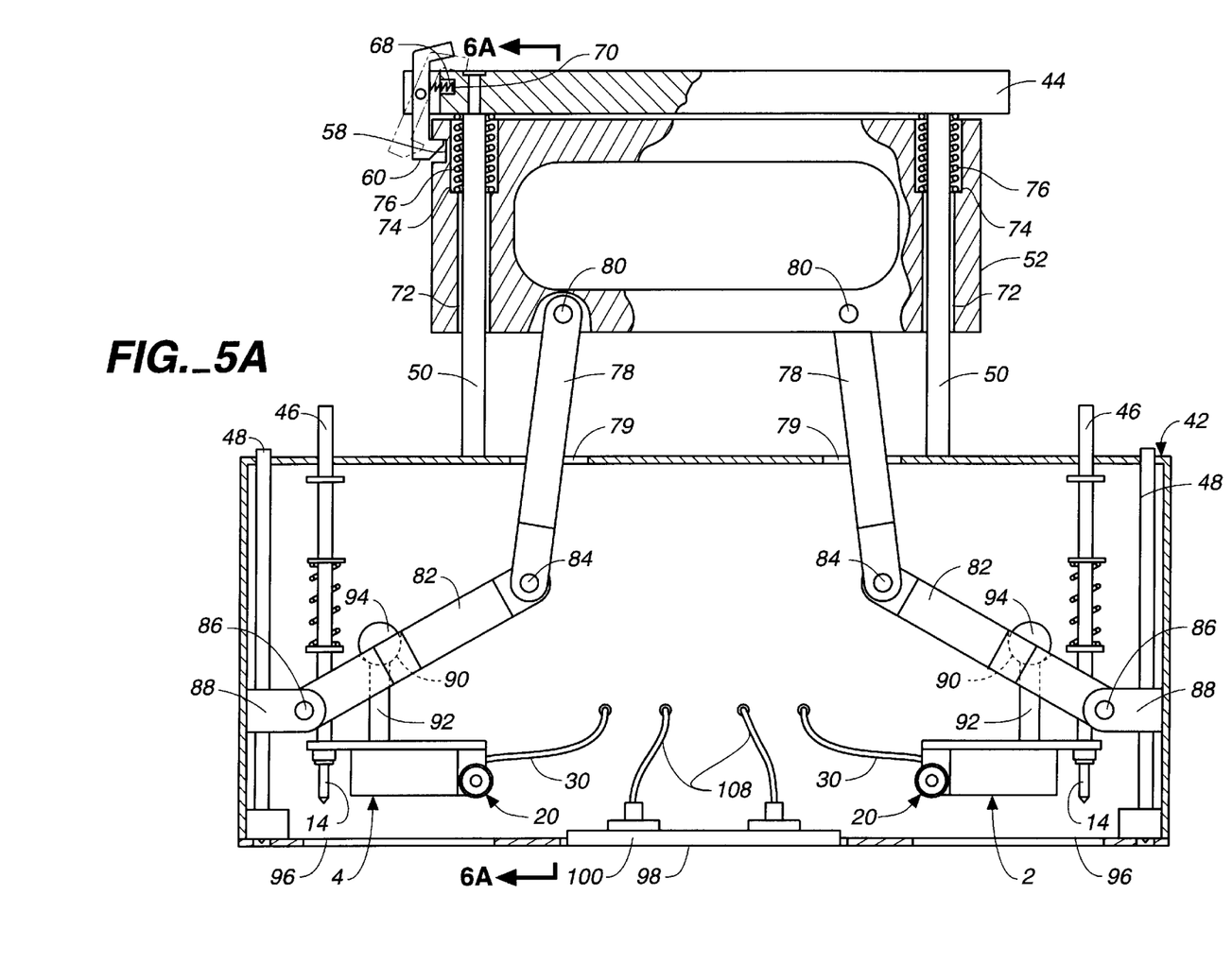
FIG. 5A is a side sectional view taken generally along line 5A—5A of FIG. 6A showing the units in the "up" position.

FIG. 5A shows handle 44 and its two slide posts 50. At one end of handle 44, latch 60 is pivotally affixed to said handle by a pin 66. Biasing latch 60 is a spring 68, extending from a small bore 70 in handle 44. Latch 60 is shown in engagement with notch 58 in slide 52. A pair of stepped bores 72 are provided in slide 52 forming a pair of shoulders 74. A pair of springs 76 bear against each shoulder 74, biasing handle 44 away from slide 52 as it travels along posts 50. Two L-shaped actuating links 78 are connected to slide 52 by a pair of pins 80. In a preferred embodiment, each actuating link 78 is L-shaped to allow positioning EMATs 2 and 4 to one side of chassis 42's longitudinal axis. Said lifting links 78 pass through a pair of slots 79 located a predetermined distance from the center of the top wall of chassis 42. A pair of Y-shaped lifting links 82 are joined to actuating links 78 by a pair of pins 84. The yoke ends of each lifting link 82 are connected by a clevis pin 86 to clevis 88, which are each affixed to chassis 42. Each lifting link 82 provides a slotted bearing surface 90. EMAT assemblies 2 and 4 are each provided with a lifting post 92 extending from plate 22 and a lifting lug 94. Lifting posts 92 pass through said slotted bearing surfaces 90 such that when lifting links 82 are raised or lowered, each of said bearing surfaces 90 engage lifting lugs 94, similarly raising or lowering each of said EMAT assemblies 2 and 4. Said raising or lowering is accomplished by the raising or lowering of slide 52 along posts 50, moving actuating links 78 attached to lifting links 82, which in turn raise or lower in pivotal rotation from clevises 88.

Further shown in FIG. 5A are several access ports, 96 and 98 located in the bottom wall of chassis 42. Access ports 96 are aligned with EMAT assemblies 2 and 4 such that when in their lowered position, they are positioned directly on the workpiece below. Access port 98 is provided near the center of the bottom wall of chassis 42 for locating temperature sensor 100, whose function is to record changes in temperature of the workpiece directly below, which changes must be factored into data transmitted by said EMATs.

Figure 5B:
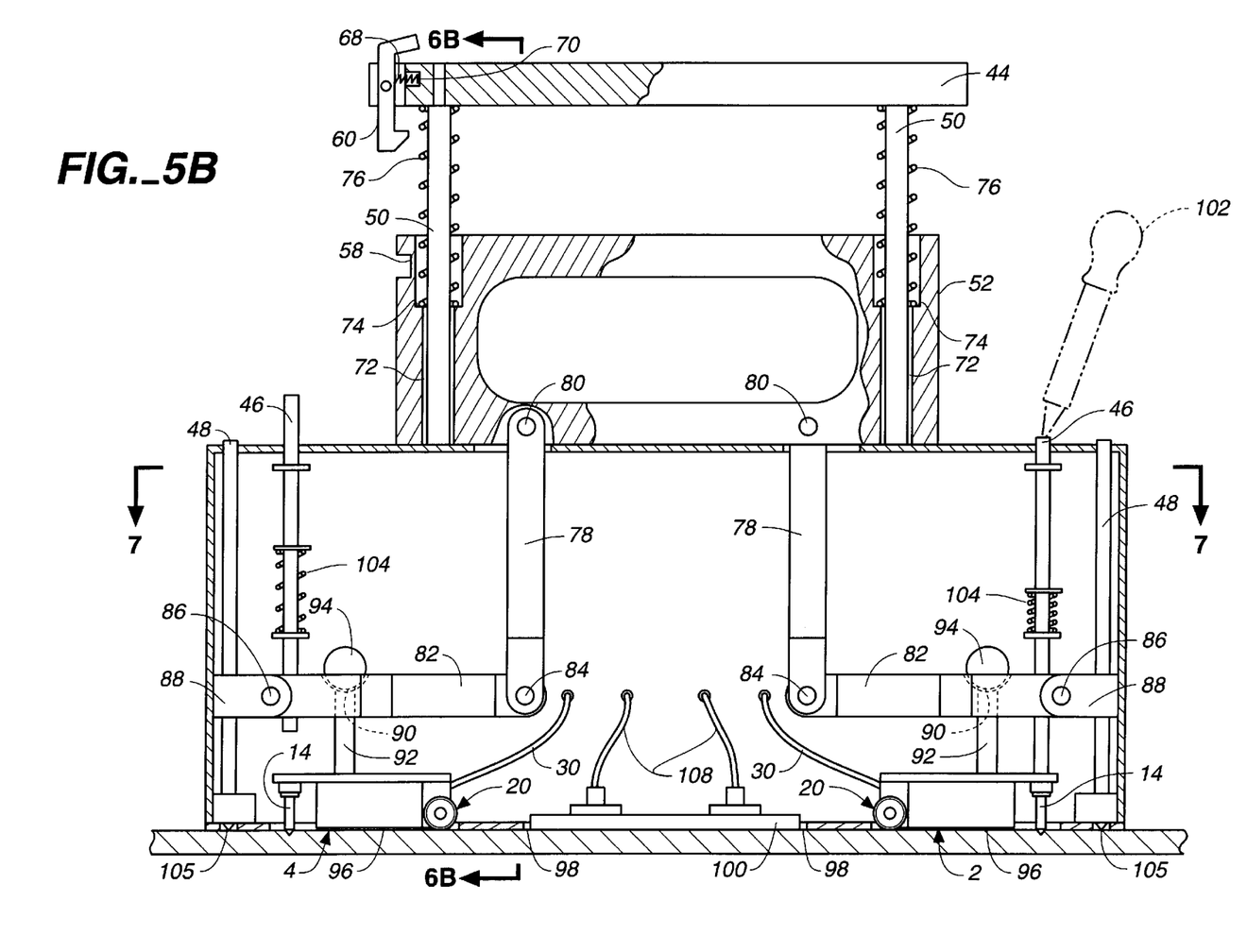
FIG. 5B is an side sectional view taken generally along line 5B—5B of FIG. 4 showing the units in the "down" position.

In FIG. 5B, EMATs 2 and 4 have been lowered into position in access ports 96, guided by lifting links 82. The position of slide 52 is shown in a direction away from handle 44, having been released by disengaging latch 60 from notch 58. Temperature sensor 100 remains in position in center access port 98 in both FIG. 5A and FIG. 5B.

The positions of retractable punch extensions 46 are also shown in FIG. 5B. Punch extension 46 located above EMAT assembly 4 is shown in the retracted state. Punch extension 46 shown in alignment with EMAT assembly 2 is compressed by striker 102 until the bottom edge of extension 46 contacts the top of positioning pin 14. Striker 102 is pressed in engagement with pin 14 until a striking force is transmitted thereto. Once struck, pin 14 extends past the bottom of chassis 42 engaging beam 6 as previously shown in FIG. 3B. Punch extension 46 retracts back into its at rest position by the force of a bias spring 104. If desired, chassis positioning pins 48 (FIG. 4) may also be struck, projecting each through chassis 42 at holes 105, anchoring chassis 42 to beam 6 in addition to EMAT assemblies 2 and 4.

Figure 6A:
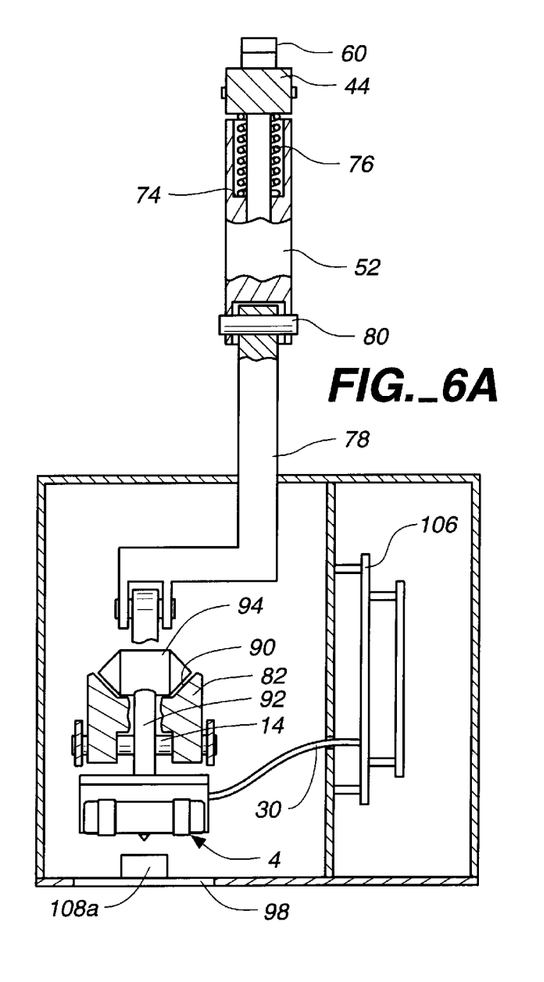
FIG. 6A is an end sectional view of FIG. 5A.
Figure 6B:
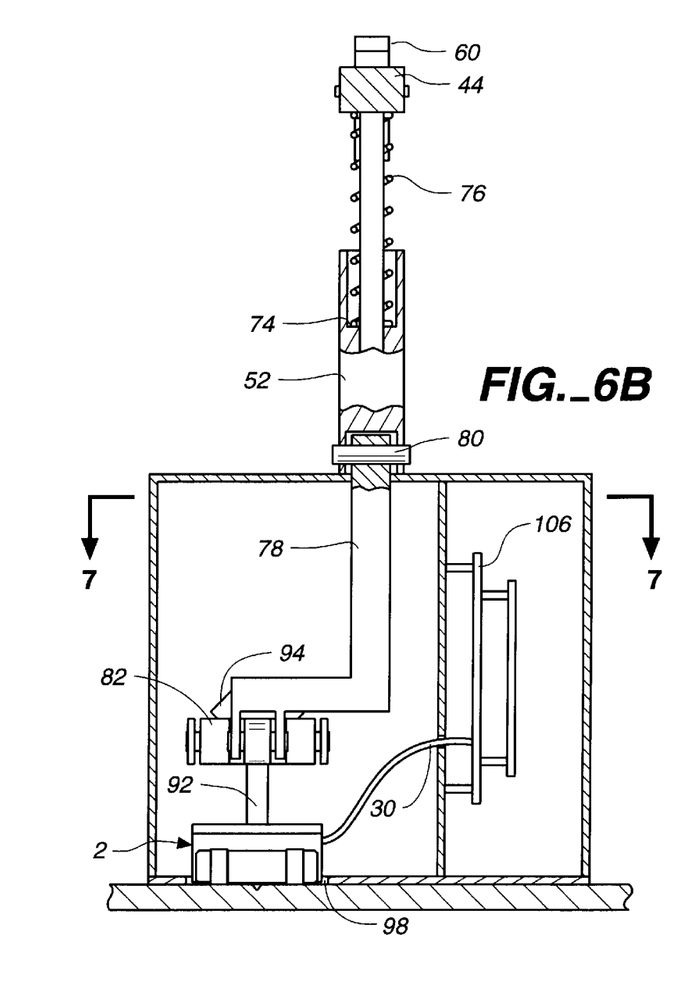
FIG. 6B is an end sectional view of FIG. 5B.

FIGS. 6A shows a sectional end view of chassis 42, particularly showing the action of slide 52 in its raised position (FIG. 6A) where lifting lug 94 is engaged in bearing surface 90 of lifting link 82. Also in this figure, the yoke configuration of lifting link 82 is shown. FIG. 6B shows EMAT 12 in the lowered position, with positioning pin 14 engaged in work piece 10.

Figure 7:
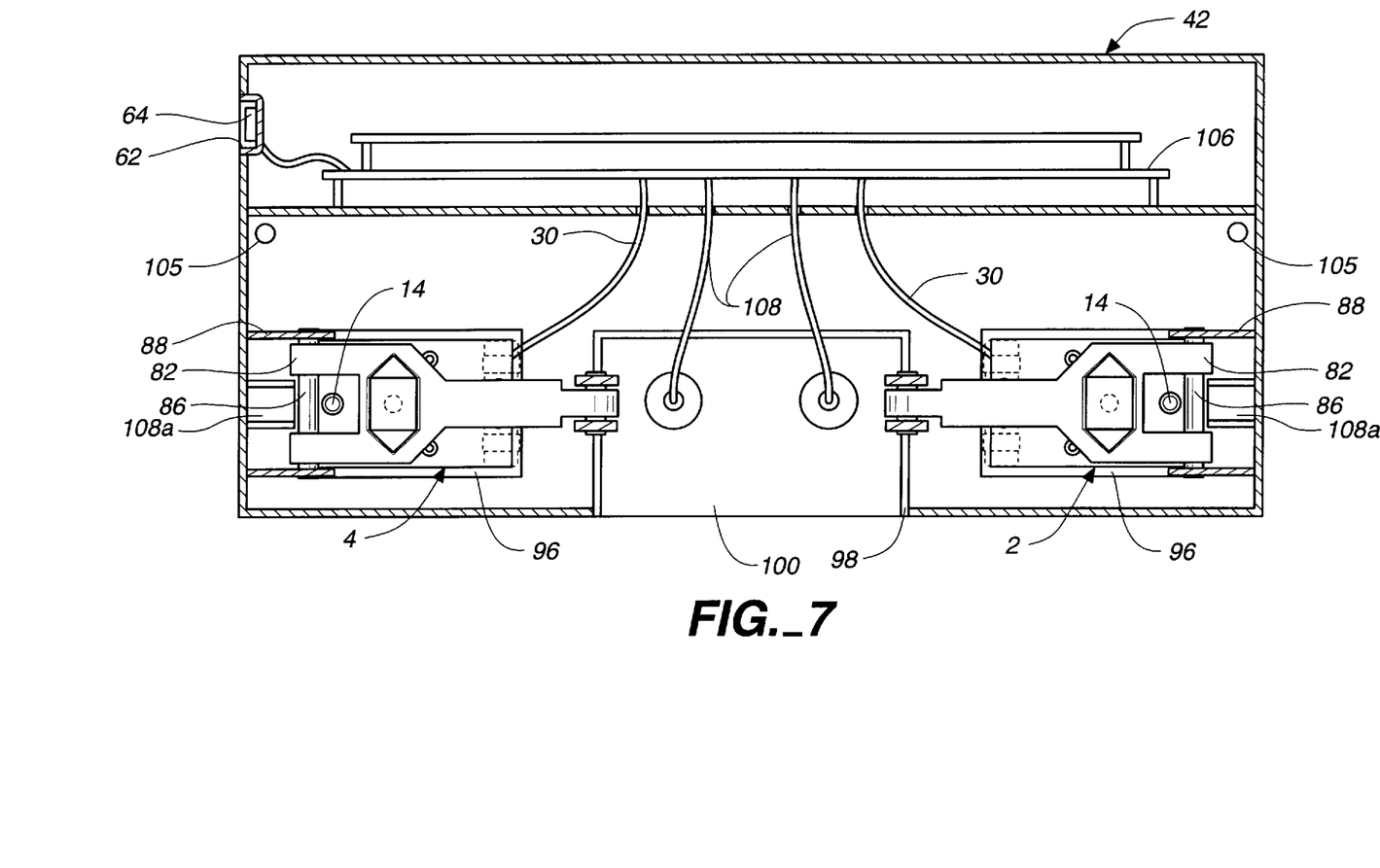
FIG. 7 is a top plan view in section taken generally along line 7—7 in FIGS. 5B and 6B.

FIG. 7 is a top plan sectional view taken at 7—7 in FIG. 5B, showing the relative positions of the internals of chassis 42. FIG. 7 shows EMATs 2 and 4 in position in access ports 96. In the present invention, bottom plane 38 of EMATs 2 and 4 (FIG. 3B) will be located substantially coplanar with beam 6 directly below, spaced in the neighborhood of 0.015" from beam 6. The dimension of 0.015" may vary according to the thickness of paint layer 8 on beam 6 (FIG. 3A). In some cases, variations in the thickness of paint layer 8 may exceed beyond 0.015" to approximately 0.030" or more. In such cases, the bottom plane of the EMAT may be spaced from beam 6 up accordingly. The farther away from beam 6, the more sensitive the EMAT must be. It is desirable to have bottom plane 38 as close to beam 6 as possible without touching said beam. In this way, unwanted frictional forces do not skew bottom plane 38, and the only contact points between EMATs 2 and 4 are wheel assemblies 20 and positioning pin 14.

Pc board 106 is shown in FIG. 7 in communication with data communication cables 30 from EMAT assemblies 2 and 4, as are also shown communication cables 108 from temperature sensor 100. Again, the yoke-like configuration of lifting link 82 is shown, as well as clevis pin 86, which pivotally affixes said lifting link to clevis 88.

In FIG. 7, holes 105 in the bottom wall of chassis 42 are shown a predetermined distance from both side walls of chassis 42. When chassis positioning pins (FIG. 4) are struck extending through holes 105, a stable footprint is established for anchoring chassis 42 and EMAT assemblies 2 and 4 to beam 6 directly below.

Figure 8:
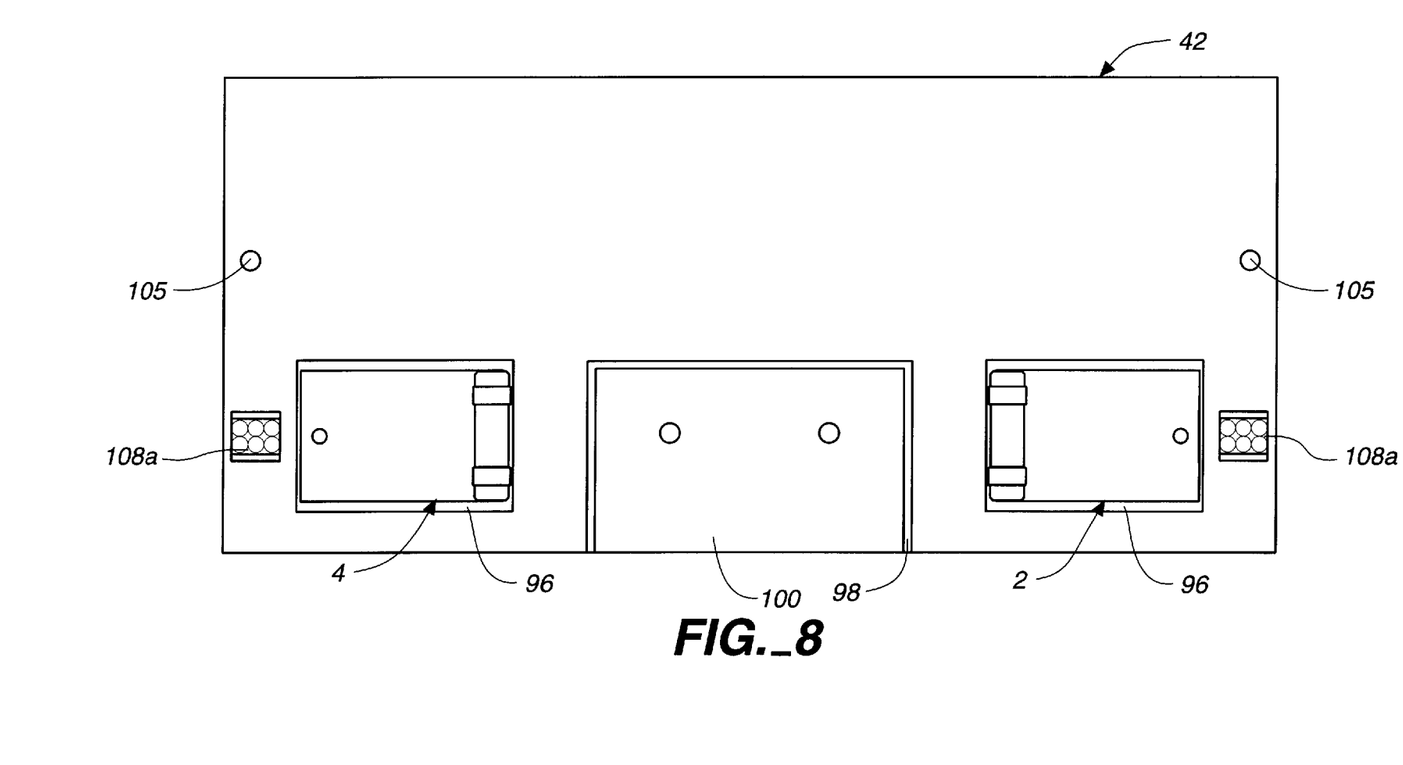
FIG. 8 is a bottom plan view of the bottom of the invention as shown in FIG. 4.

FIG. 8 further shows the layout of the bottom wall of chassis 42. Relative positions of access ports 96 and 98 are seen as well as holes 105. The location of two magnet ports 108 for initially positioning chassis 48 on a beam are also shown. The magnets provided in the base of chassis 42 are used to initially secure chassis 42 to beam 6 prior to positioning the EMATs or anchoring the chassis.

While the invention has been described in connection with what is presently considered the most practical and preferred embodiment(s), it is to be understood that the invention is not limited to the disclosed embodiment(s) but, on the contrary is intended to cover various modifications and equivalent arrangements included within the scope of the appended claims.

What is claimed is:

1. An improved apparatus capable of transmitting and receiving acoustic waves through a workpiece comprising:
    a pair of Electromagnetic Acoustic Transducers ("EMATs") for respectively transmitting and receiving acoustic waves through said workpiece and for determining the applied strain in the workpiece by measuring the change in time of flight between the workpiece in the stressed and unstressed condition for determining applied strain;
    an EMAT body for each of said EMATs, each of said bodies having a bottom plane and a longitudinal axis;
    a pin fixed relative to each of said bodies' longitudinal axis, said pin extending a first predetermined distance beyond said plane for engaging the workpiece to fix the position of said body with respect thereto and to maintain the coplanar registry between each EMAT and the workpiece at a second predetermined distance, said pin having an upper end for striking and a hardened pointed end for engaging the workpiece;
    a friction reducing means affixed to each of said bodies for engaging the workpiece and supporting said EMAT thereon such that when said pin is struck thereby indenting said workpiece and locating said bottom plane in substantially coplanar registry therewith, surface deformations occurring in said workpiece have negligible effect on said body's position thereon and for allowing deformation of the workpiece under each EMAT without compromising the registry between the pair of EMAT's.

2. The device as described in claim 1 wherein:
    said friction reducing means comprises a wheel assembly.

3. The device as described in claim 1 wherein:
    said friction reducing means comprises at least one roller bearing affixed to said EMAT body.

4. The device as described in claim 1 wherein:
    the distance between said bottom plane and said workpiece approximates 0.015".

5. An improved Electromagnetic Acoustic Transducer ("EMAT") for transmitting or receiving acoustic waves through a workpiece comprising:
    an EMAT having a magnetic body with a bottom plane and a data transmission cable, said body having an extended portion on one end;
    said portion having a top surface, a bottom surface, a rear surface and two side surfaces, said top surface forming a groove for guiding said cable from said EMAT, said side surfaces each having a tapped hole;
    a first plate affixed to said portion covering said groove and said cable;
    a steel second plate affixed to and extending beyond said EMAT, said second plate having a threaded hole therethrough, said threaded hole being positioned in alignment with the longitudinal axis of said EMAT;
    a pair of wheel bearings;
    a pair of screws, each of said screws passing through the center of one of said wheel bearings, each of said screws engaged in each of the tapped holes retaining said wheel bearings proximate to said portion such that when at rest, said EMAT'S bottom plane is substantially parallel with said workpiece; and
    a positioning pin comprising a threaded punch engaged in said steel second plate's threaded hole and extending a first predetermined distance beyond said bottom plane, said pin having an upper end for striking and a hardened pointed lower end, such that when said EMATs are placed upon the workpiece, striking said pin drives said pin into the workpiece thereby retaining said EMATs in coplanar registration therewith at a second predetermined distance from the workpiece.

6. The device of claim 5 wherein:

said bottom plane is located approximately 0.015" from said workpiece after striking said positioning pin.

7. An apparatus capable of continually monitoring stress in a workpiece comprising:

a chassis;

a pair of Electromagnetic Acoustic Transducers ("EMATs") for respectively transmitting and receiving acoustic waves through said workpiece and for determining the applied strain in the workpiece by measuring the change in time of flight between the workpiece in the stressed and unstressed condition for determining applied strain, each of said EMATs comprising a body having a bottom plane and a longitudinal axis, a pin fixed relative to said body aligned with said body's longitudinal axis, said pin extending a first predetermined distance beyond said pin having an upper end for striking and a pointed end for engaging said workpiece to fix the position of said body with respect thereto and to maintain the coplanar registry between each EMAT and the workpiece at a second predetermined distance, and friction reducing means affixed to said body for engaging said workpiece and supporting said EMAT thereon and for allowing deformation of the workpiece under each EMAT without compromising the registry between the two EMAT's;

a mechanism affixed in said chassis, said mechanism operably connected to said EMATs such that said mechanism raises and lowers said EMATs onto said workpiece; and means for actuating said mechanism.

8. The apparatus as described in claim 7 wherein:

said mechanism comprises a series of links connected to said chassis and said actuating mechanism.

9. The apparatus as described in claim 7 wherein:

said actuating means comprises a handle in combination with a slide, said slide operably connected with said mechanism.

10. The apparatus as described in claim 7 wherein:

said actuating means is electronically operated.

11. The apparatus as described in claim 7 wherein:

said mechanism is electronically operated.

12. An apparatus for positioning more than one EMAT above a workpiece comprising:

a box-like chassis, said chassis having a top wall, a bottom wall, two end walls and two side walls, said top wall having two slots spaced at a predetermined distance from the center of said chassis, said top wall having two first holes proximate to the longitudinal axis of said chassis and said end walls, said top wall having two second holes parallel to said longitudinal axis and located a predetermined distance from said end walls, said bottom wall having two access ports parallel to said longitudinal axis and positioned on either side of a third access port, said bottom wall having two holes directly below and in registry with said top wall's two first holes, one of said end walls forming a slot for a PC interface connector, said bottom wall having two rectangular holes proximate to said end walls;

a pair of magnets affixed in said rectangular holes;

a pair of positioning pins extending through said first holes in said top wall and said corresponding holes in said bottom wall, said first positioning pins having a top end for striking and a bottom pointed end, said first positioning pins rigidly affixed to said chassis;

a handle with two downward projecting posts;

a slide of generally rectangular shape and forming a grip, said slide having a pair of stepped bores each forming a shoulder, said slide having a notch on one end, said slide having two throughholes across its width and proximate to its bottom edge;

said handle and said posts passing through said slide, said posts affixed to said top wall of said chassis;

a pair of first springs located in said stepped bores and bearing against said shoulders of said handle, thereby biasing said handle away from said slide;

a latch, pivotally affixed to said handle and biased toward said notch by a second spring, said latch engageable with said notch for retaining said slide proximate to said handle;

a pair of L-shaped actuating links passing through said slots, said actuating links each having a first hole at one end of said links and a second hole at the opposite end of said links;

a first pair of link pins passing through said first holes of said actuating links and said throughholes of said slide thereby rotatably affixing said actuating links to said slide;

a pair of Y-shaped lifting links having a singular end and two yoke ends opposite said singular end, each of said lifting links having a slotted bearing surface proximate to said yoke ends, said lifting links each having a hole in each of said ends;

a pair of clevises each affixed to an inside of said end walls at a predetermined distance from said bottom wall, said clevises having a cross beam with a throughhole in alignment with said top wall's second holes, each of said clevises having a hole therethrough;

a pair of clevis pins, said clevis pins passing through said clevises and said yoke ends of said lifting links pivotally affixing said lifting links to said clevises;

a second pair of link pins passing through said single ends of said lifting links and said second holes in said actuating links pivotally affixing said lifting links to said actuating links;

at least one PC board affixed to said bottom wall of said chassis;

a cable connector affixed in said slot in said end wall, said connector in communication with said PC board;

a temperature sensor affixed in said third access port, said temperature sensor having a cable in communication with said PC board;

a pair of EMATs as described in claim 1, said EMATs having a lifting post, said lifting posts passing through said slots in said lifting links, said cables in communication with said PC board, said EMATs positioned a predetermined distance above said access ports;

a pair of retractable punch extensions extending vertically downward from said second holes in said top wall through said throughhole in said cross beam and in engageable alignment with said pins in said EMATs; and each of said lifting posts having attached thereto a lifting lug, such that when said grip is squeezed, drawing said slide toward said handle, said actuating links move said lifting links upward, engaging said lifting lugs in said slotted bearing surface thereby drawing said EMATs away from said access ports, and conversely, when said latch is disengaged from said notch allowing said spring to bias said slide away from said handle, said actuating links move said lifting links downward, thereby lowering said EMATs by said lifting lugs until said EMATs are proximate to said access ports and thereby, to said workpiece so that when external force is applied to said positioning pins, said chassis is located in registry with said workpiece, and when external force is applied to said punch pin extensions, said pins of said EMATs locate said EMATs in registry with said workpiece.

* * * * *